United States Patent [19]

Nelson

[11] 4,275,725
[45] Jun. 30, 1981

[54] BREATHING APPARATUS

[76] Inventor: Byron G. Nelson, P.O. Box 6457, Lake Charles, La. 70606

[21] Appl. No.: 99,855

[22] Filed: Dec. 3, 1979

[51] Int. Cl.³ ............................................. A61M 15/00
[52] U.S. Cl. ................................. 128/207.14; 128/136
[58] Field of Search ...................... 128/202.28, 203.12, 128/203.23, 203.24, 204.13, 207.14, 136, 205.27, 202.21, 200.24, 203.15; 131/190, 191; 433/91, 93, 140

[56] References Cited
U.S. PATENT DOCUMENTS 3,106,916  10/1963  Matthes ........................... 128/202.28

Primary Examiner—Henry J. Recla

[57] ABSTRACT

An improved breathing apparatus fittable into the mouth of a human between the teeth and cheek is disclosed. The apparatus comprises a tube having a front opening and a back opening and sufficient length to project forward to the front of the lips and rearward down the side of the mouth to a point adjacent the molars; to the end of the tube proximate the exterior of the lips is coupled a curved flange stabilizing means and spaced rearward of the curved flange stabilizing means is curved sealing means adapted to fit between the frontal teeth and the lips to an extent to seal off passage of air through the mouth except into the tube.

10 Claims, 9 Drawing Figures

U.S. Patent    Jun. 30, 1981    4,275,725
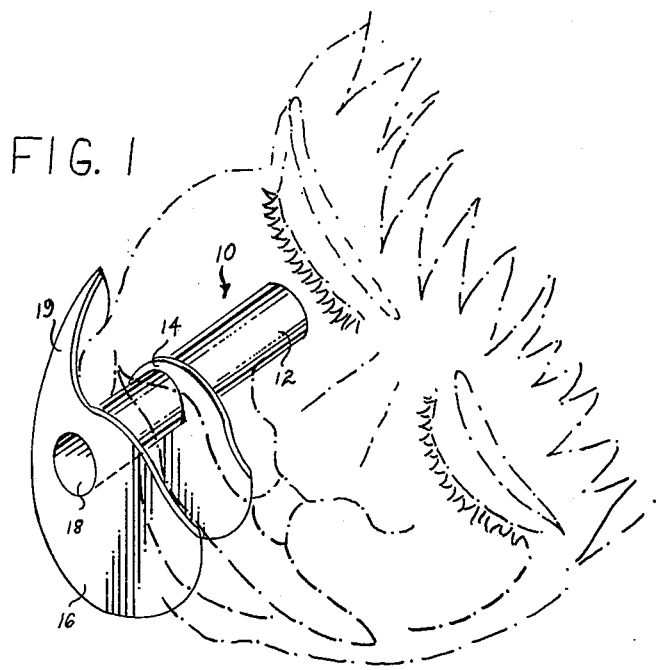
FIG. 1
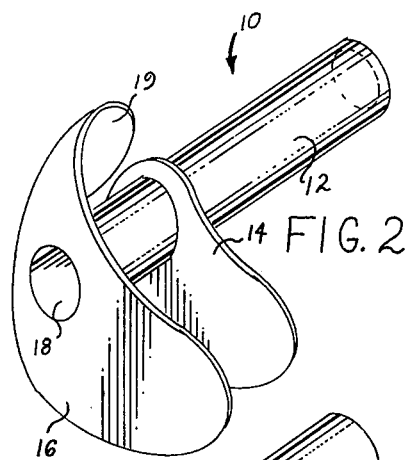
FIG. 2
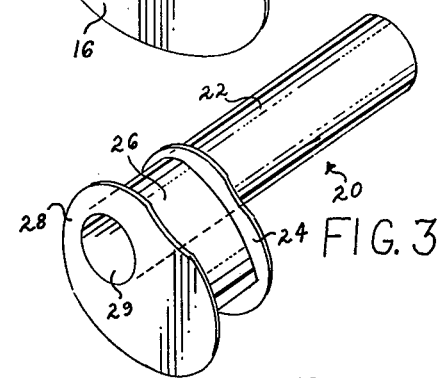
FIG. 3
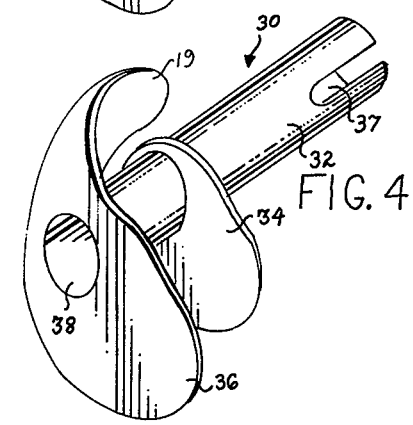
FIG. 4
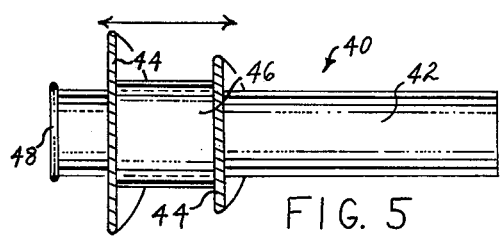
FIG. 5
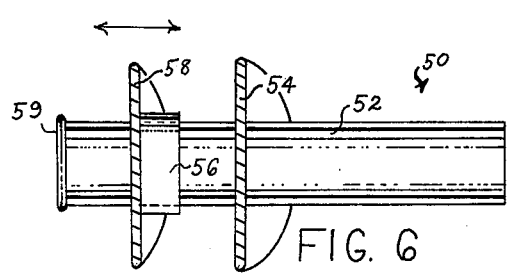
FIG. 6
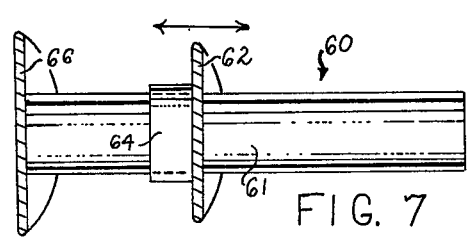
FIG. 7
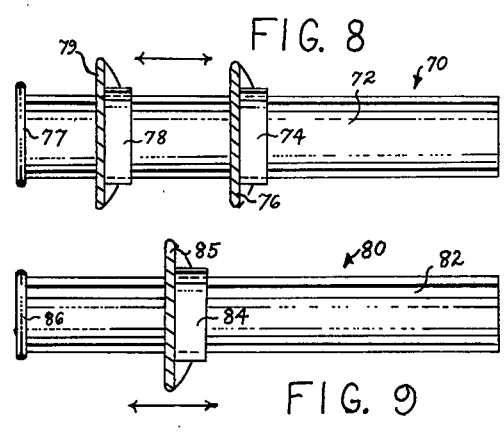
FIG. 8
FIG. 9

BREATHING APPARATUS

Patent application Ser. Nos. 97,325 and 89,035 and 88,043 are related cross references.

BACKGROUND OF THE INVENTION

There are many people who are bothered with a nasal blockage which hinders their breathing, especially at night when they are attempting to sleep. A nasal blockage can either be in one or both nostrils, but in either case the sufferer usually ends up breathing through his or her mouth. Mouth breathing is recognized as being unhealthy as it contributes to the development of gum diseases such as pyorrhea.

It is therefore an object of this invention to provide an improved breathing apparatus of the kind which the user can wear inside of the mouth between the cheek and teeth to allow the user to safely breathe through his or her mouth without drying out the mouth or causing gum disease problems. While accomplishing these advantages, it is another object of this invention to allow for freedom of tongue, lip and jaw movement by reason of improved lateral and vertical stabilization in the area of the lips; these movements are essential in effecting comfortable, safe, respiration and in effecting the salivation adjusting function of swallowing.

Yet another object of this invention is to provide a breathing apparatus which allows an ease in verbal conversation on the part of the user without having to remove the apparatus from the mouth.

THE INVENTION

This invention relates to an improvement in a breathing apparatus of the kind which is fittable into the mouth of a human between the cheek and teeth and which is comprised of a tube having a front opening and a back opening and having sufficient length to extend from the front of the mouth rearward to a point adjacent the molars, and having curved sealing means which fits behind the lips and in front of the teeth which prevents air from entering the mouth except into the tube of the apparatus; the improvement being curved external stabilizing flange means coupled to an extension of the tube of the apparatus such that the curved external stabilizer flange will be situated outside of and proximate the lips and approximately parallel to the curved sealing means so that there will be improved stabilization and safety from swallowing the apparatus when the breathing apparatus is in position in the mouth of the user.

As can be seen from the above, the apparatus of this invention, when in the human mouth will assist in the direction of air from the front of the mouth to the rear portion of the mouth and on down to the trachea. By routing the air to the rear of the mouth, the user of the apparatus safely and comfortably avoids exposing much of his or her mouth to the drying and deleterious effects of an otherwise uncontained air passage over and through the several parts of the mouth.

These and other features contributing satisfaction in use and economy in manufacture will be more fully understood from the following description of preferred embodiments of the invention when taken in connection with the accompanying drawings in which identical numerals refer to identical parts and in which:

FIG. 1—is a view of one embodiment of this invention positioned in a human mouth;

FIG. 2—is a perspective view of a second embodiment of this invention;

FIG. 3—is a perspective view of a third embodiment of this invention;

FIG. 4—is a perspective view of a fourth embodiment of this invention;

FIG. 5—is a side elevational view of a fifth embodiment of the invention with curved stabilizer and curved seal portions cut away;

FIG. 6—is a side elevational view of a sixth embodiment of the invention with curved stabilizer and curved seal portions cut away;

FIG. 7—is a side elevational view of a seventh embodiment of the invention with curved stabilizer and curved seal portions cut away;

FIG. 8—is a side elevational view of an eighth embodiment of the invention with curved stabilizer and curved seal portions cut away; and, FIG. 9—is a side elevational view of a ninth embodiment of the invention with curved stabilizer or curved seal partially cut away.

Referring now to the FIGS. 1-2, there is shown an embodiment of this invention, generally designated by the numeral 10, having hollow tube means 12 with a rigidly affixed curved flange stabilizing means 16 at the end of tube means 12 which will be approximate the lips as is shown in FIG. 1. The purpose of this curved flange stabilizer means 16 is to assist in the stabilization of the tube means 12 when in position in the mouth, thus increasing safety from swallowing and comfort in wearing. Immediately rearward of curved flange stabilizing means 16 there is curved sealing means 14 which is also rigidly affixed to tube means 12. The spacing between flange stabilizing means 16 and curved sealing means 14 is such that the user's lips will comfortably fit in between as is seen in FIG. 1. The aperture 18 at the proximate end of the tube 12 is dimensioned of a size to allow sufficient air to be breathed by the user under normal breathing conditions. Additional curved portion 19 is affixed to curved flange stabilizing means 16 and is adapted to follow the contours of the exterior of the user's mouth and cheek, thus providing great comfort and safety to the user from swallowing the apparatus.

Curved flange stabilizer means 16 and curved sealing means 14 are approximately parallel and each is adapted to follow the general contours of the frontal mouth when the apparatus is in position in the mouth. Having curved flange stabilizing means 16 and curved sealing means 14 to follow natural curvature of the human mouth provides comfort and stabilized fit to the user.

In FIG. 3, a second embodiment of a breathing apparatus of this invention, generally designated by the numeral 20, is shown. Apparatus 20 has a hollow tube means 22 and at its proximate end is curved flange means stabilizer 28 and curved sealing means 24. As seen in FIG. 3, when viewed in front elevation, there is provided in the space between curved flange stabilizer means 28 and curved sealing means 24 tube means extension 26 which follows a pear shape configuration. The purpose of having a pear shape configuration of tube means extension 26 is to provide comfort in use for the user when the user wishes to engage in speaking while the apparatus is in position in the mouth. The more obtuse side of the pear shape extension will nest comfortably in the corner of the mouth providing both stability and partial sealing. Aperture 29 is dimensioned the same as aperture 18.

Another embodiment shown in FIG. 4, generally designated by the numeral 30, has an elongated hollow tube means 32. At the proximate end of hollow tube means 32 there is provided curved flange stabilizer means 36 and curved sealing means 34. Curved flange stabilizer means 36 has the additional curved portion 19 which is adapted to follow the contours of the exterior of the user's mouth and cheek, for greater comfort and safety. Note also that tube means 32 has a side facing opening 37 which allows air to be drawn through aperture 38 and enter into the mouth at least in part from a sideways direction.

Another embodiment designated by the numeral 40 is shown in FIG. 5. This embodiment has hollow tube means 42 having at its proximate end a stopping bead 48. Slidably mounted on hollow tube means 42 is collar 46 which has a diameter slightly smaller than the diameter of bead 48 thereby preventing collar 46 from over-riding bead 48. Integrally formed with collar 46 are curved flanges 44. As can be appreciated, in this embodiment, curved flanges 44 are axially movable about tube 42 thereby allowing the user to adjust the depth into his or her mouth into which tube means 42 shall extend. While stopping bead 48 is shown circumscribing tube 42, it is to be understood that stopping bead 48 may occupy only so much area of tube 42 necessary to prevent collar 46 from over-riding bead 48.

In FIG. 6 another embodiment is shown, generally designated by numeral 50. Embodiment 50 has an elongated hollow tube 52 which has at its proximate end stopping bead 59. Rearward of bead 59 there is provided curved sealing means 54 which is rigidly affixed to tube 52. Between bead 59 and curved sealing means 54 there is slidably mounted thereto collar 56 which carries curved flange 58. By having curved flange 58 adjustable between bead 59 and curved sealing means 54, the user may adjust the distance between the curved flange 58 and curved sealing means 54 to accommodate the width of the user's lips.

In FIG. 6 another embodiment is shown, generally designated by the numeral 60, which enables the user to adjust the width between curved flange and curved sealing means for lip comfort. Embodiment 60 has an elongated hollow tube means 61 having permanently affixed to its proximate end curved flange means 66. Slidably mounted on tube 61 is collar 64 having integrally formed therewith curved sealing means 62. As can be appreciated, curved sealing means 62 can be moved frontward or rearward to fit the user's lips.

In FIG. 8 another embodiment is shown, generally designated by the numeral 70, which incorporates adjustment for thickness of the user's lips and also the depth of the user's mouth. Embodiment 70 has a hollow tube 72 with stopping bead 77 about its proximate end. Slidably mounted on tube 72 are collars 74 and 78. Collar 74 has curved sealing means 76 integrally formed therewith, while collar 78 has curved flange 79 integrally formed therewith. Diameters of collars 78 and 74 are smaller than the bead 77 thereby preventing the removal of collars 74 and 78 from the tube 72 by passage over bead 77. As can be seen, the user can adjust the distance between curved flange 79 and curved sealing means 76 for lip comfort and at the same time adjust the depth of tube 72 as it fits into the interior of the user's mouth.

In FIG. 9 another embodiment is shown, generally designated by the numeral 80. This embodiment allows for adjustment of the depth which elongated hollow tube will fit into the user's mouth. Slidably mounted about tube 82 is collar 84 with an integrally formed curved flange 85. At the proximate end of tube 82 there is provided stopping bead 86 which has a diameter greater than the diameter of collar 84. Curved flange 85 will fit on the exterior of the lips or may be adapted to fit between teeth and lips. It is easy to see in FIG. 9 how the depth of tube 82 can be adjusted so that it will fit to a depth in the user's mouth which is comfortable for him or her.

In all of the embodiments shown the length of the hollow tube means should be such that it will be capable of extending beyond the front tooth line rearward to a point adjacent the molars. In the adjustable embodiments, i.e. embodiments shown in FIGS. 5,6,7,8, and 9, the length of the tube is not as critical as with the fixed flange embodiment shown in FIGS. 2-4 as the user can adjust the depth to which the tube extends into the user's mouth. It is expected that the tube may be of a shape cross-section wise such that it will fit not only between the teeth and cheek, but also, possibly between the teeth, gums, and cheek.

The breathing apparatuses of this invention may be made of any convenient material which is inert in the human mouth. The material may be either flexible or rigid. An example of a flexible useful material is latex rubber and other plastics which are presently used in the medical field and which are inert, as mentioned previously. Rigid materials such as high density polyethylene, polypropylene, etc. may be utilized.

Manufacture of the breathing apparatus of this invention can be achieved by conventional molding procedures well known to those skilled in the art.

It can be appreciated from the foregoing that the above embodiments of this invention provide the user with both safe and comfortable means for breathing through his or her mouth. Due to the variability of the tube length, it is possible to have the tube extend to the rearmost portion of the side of the user's mouth or to a point along the molar line. Thus, the relatively dry air which is inhaled is routed around the saliva glands and gums and does not become an irritant thereto; the saliva which would otherwise be evaporated by an uncontained air flow will as a result of the use of this apparatus improvement, remain available for lubricating the separate parts of the mouth and tongue as well as the laryngeal area of the trachea.

Not only is there a positive effect from utilizing the apparatus of this invention, the apparatus is also safe and comfortable to wear as it allows for free movement of lips, tongue and jaws, the free movement thereby effecting an ease in the salivation adjusting function of swallowing, as well as an ease of oral communication.

What is claimed is:

1. In a breathing apparatus of the kind which is fittable in the mouth of a human between the cheek and teeth, which apparatus includes tube means having an opening proximate to the lips and an opening distal to the lips, said distal opening adapted to be located proximate the molars, said openings being sized in combination to permit a flow of respirated air through said tube means approximate the flow of air said human could achieve through normal nasal breathing; said tube means being adapted and having sufficient length to extend from the front of said mouth back down the side of said mouth to a point adjacent the molars, and sealing means adapted to extend from said front open end around the front of said mouth to an extent to seal off passage of air through said front of said mouth except into said front opening, said sealing means being adapted for fitment between the frontal teeth and lips; an improvement comprising flange stabilizer means coupled to an extension of said tube means at a point forward of said sealing means, said flange stabilizer means being adapted for fitment along the exterior of said lips when said apparatus is in the mouth, said flange stabilizer means being in a plane approximately parallel to the plane of said sealing means, the space between said flange stabilizer means and said sealing means being approximate the width of said human's lips.

2. The improvement of claim 1 wherein said flange stabilizer means is rigidly affixed to said tube means.

3. The improvement of claim 1 wherein said flange stabilizer means is axially movable along said tube means.

4. The improvement of claim 3 wherein there is additionally provided stopping means adjacent the front open end of said extension of said tube means, said stopping means being adapted to prevent unwanted removal of said flange stabilizer means at the front of said extension.

5. The improvement of claim 1 wherein said extension of said tube means between said flange stabilizer means and said curved sealing means has a pear shape configuration whereby the more obtuse end of said pear shaped extension is adapted to fit in the corner of the user's mouth.

6. The improvement of claim 1 wherein said flange stabilizer means has an additional portion adapted for fitment around the outside of the cheek of the user's mouth.

7. The improvement of claim 1 wherein said sealing means and said flange stabilizer means are both axially movable along said tube means.

8. The improvement of claim 7 wherein there is additionally provided a stopping means adjacent the front opening of said extension of said tube means, said stopping means being adapted to prevent unwanted removal of said flange stabilizer means and said curved sealing means from the front of said tube means.

9. In a breathing apparatus of the kind which is fittable in the mouth of a human between the cheek and teeth, which apparatus includes tube means having an opening proximate the lips and an opening distal to the lips, said distal opening adapted to be located proximate the molars; said openings being sized in combination to permit a flow of respirated air through said tube means approximate the flow of air said human could achieve through normal nasal breathing; said tube means being adapted and having sufficient length to extend from the front of said mouth back down the side of said mouth to a point adjacent the molars, and sealing means adapted to extend from said tube means and adapted for fitment between the frontal teeth and lips; an improvement wherein said sealing means is axially movable along said tube means.

10. In a breathing apparatus of the kind which is fittable in the mouth of a human between the cheek and teeth, which apparatus includes tube means having an opening proximate to the lips and an opening distal to the lips, said distal opening adapted to be located proximate the molars, said openings being sized in combination to permit a flow of air approximate that flow of air said human could achieve through normal nasal breathing; said tube means being adapted and having sufficient length to extend from the front of said mouth back down the side of said mouth to a point adjacent the molars, and flange stabilizing means extending from said tube means, said stabilizing means being adapted for fitment externally proximate the lips; an improvement wherein said flange stabilizing means is axially movable along said tube means.

* * * * *